United States Patent
Han et al.

(10) Patent No.: US 7,363,088 B2
(45) Date of Patent: Apr. 22, 2008

(54) HUMAN-BODY POTENTIAL CONTROLLING ELECTROTHERAPEUTIC DEVICE

(76) Inventors: Hak Ja Han, #72-2, Cheongpa-Dong 1-Ga, Yongsan-Gu, Seoul 140-131 (KR); Jung Soon Cho, 101-904 Hongeun Geugdong Apartment, 454, 38/1, Hongeun-Dong, Seodaemoon-Gu, Seoul 120-773 (KR)

( * ) Notice: Subject to any disclaimer, the term of this patent is extended or adjusted under 35 U.S.C. 154(b) by 462 days.

(21) Appl. No.: 10/345,784

(22) Filed: Jan. 16, 2003

(65) Prior Publication Data
US 2003/0158590 A1    Aug. 21, 2003

(30) Foreign Application Priority Data
Feb. 15, 2002    (KR)    ................................. 2002-8257
Nov. 29, 2002   (KR)    ............................... 2002-75252

(51) Int. Cl.
*A61N 1/00*    (2006.01)
(52) U.S. Cl. ....................................................... 607/74
(58) Field of Classification Search .................... 607/2, 607/63–71, 76
See application file for complete search history.

(56) References Cited
U.S. PATENT DOCUMENTS
3,648,708 A * 3/1972 Haeri ........................... 607/64
5,800,477 A * 9/1998 Groux .......................... 607/76

OTHER PUBLICATIONS
Zhong (CN 1327857A), Multifunctional Teraputic Apparatus (Jun. 20, 2001), Derwent.*

\* cited by examiner

*Primary Examiner*—George Manuel
(74) *Attorney, Agent, or Firm*—Lee, Hong, Degerman, Kang & Schmadeka

(57) ABSTRACT

An electrotherapeutic device for simultaneously generating positive, negative, or multiple polarities. The device includes a power source section and pulse generating sections for inputting prescribed high-voltage oscillating frequency signals to bipolar output sections. The bipolar output section can select poles according to a switching operation after amplifying and waveform-shaping the signals emitted from the pulse generating sections. Also, the device includes an operating time controlling section with alarm function. Thus, the bipolar electrotherapeutic device pulses currents of positive(+) and negative(−) poles or multiple poles(+, −, +, −, +) without short circuiting to allow for safe use in seeking abnormal areas in a human body to control and remove accumulated anions and cations.

5 Claims, 10 Drawing Sheets

HUMAN-BODY POTENTIAL CONTROLLING ELECTROTHERAPEUTIC DEVICE

FIELD OF THE INVENTION

The present invention relates to an electrotherapeutic device and more particularly to human-body potential controlling electrotherapeutic device capable of simultaneously generating positive(+), negative(−) or multiple polarities(+, −, +, −,).

BACKGROUND OF THE INVENTION

The human-body potential controlling electrotherapeutic device according to the present invention is provided with mutually independent circuits so that a simultaneous contact of any outputting poles taken from respective positive(+) and/or negative(−) pole sources and/or multiple pole sources including a number of (+) and (−) poles results in minimized or seldom short-circuit.

Accordingly even a simultaneous use of positive and negative poles onto human skin tissues guarantees safety.

In the morbid areas of a human body there are cations and anions in their incomplete state, originated from metabolic products, wherein cations are augmented together with other cations and anions are augmented together with other anions. These interfere with the normal blood flow causing extravasated blood or blood congestion, whereby both capillary vessels and nerve tissues are suppressed, causing the lacking supply of nutritious substance and oxygen. These morbid areas become habitats for bacteria leading to various diseases. Likewise, when cations and anions are accumulated excessively either outside or inside the cellular membranes, potential difference and therewith tension are increased ultimately to cause diseases.

The reason why the ions or pre-ions with the equal polarity in their incomplete or metastable state as described above flock together is believed to be owing to the failure in finding their counter ions they desire, such as electrons or protons. The incompleteness may induce the particles of identical polarity to aggregate to a larger cluster until they meet with counterparts, however they stay flocked together no more, once they meet true counterparts with opposite polarity due to the electric repulsive force between equal polarities.

Therefore, the electrons and protons generated from the therapeutic device according to the invention are expected to seek the balance between ions by the dual characteristics to promote combination, neutralization and dissolution through inter-polar reciprocal action, namely give and take action, with the incomplete ions on the morbid areas of a human body.

When a balance between incomplete ions is established, the dissolution of the inflammatory products on the morbid areas may be accelerated and cells as well as tissues may be regenerated as normal. Further, instant neutralization heat is generated in the course of binding and neutralizing between the elements generated by the inventive therapeutic device and physical incomplete ions, causing disinfecting action. Accordingly, the recovery in the regulating function and immunity function of a human body itself can be expected, so that the diseases may be eliminated or may be prevented.

The conventional electrotherapeutic apparatuses include physical treating devices based on high, medium and low frequency, employing direct(DC), alternating(AC) or pulsating current(PC), wherein the positive(+) and negative(−) poles derived from the devices produce the action of short circuit in human body as a conductor due to their compatible relation. A simple action as an electric conductor without the intimate mutual relation with the morbid areas on human body prevents the disease causing materials from being removed. Thus, substantially no other effect than temporary physical effect through heat, vibration or stimulus could be attained with those conventional treating devices, even risking the human bodies depending on the cases.

Although single-pole therapeutic devices were introduced recently to resolve the problem as described above, the use of only one pole out of two electric poles has the disadvantage that one-sided change in human body is induced even to bring forth a potential imbalance in tissues and cells.

Accordingly, the originally intended goal of curing diseases was hardly achieved with the conventional therapeutic apparatuses mainly because the ionic imbalance representing the fundamental source of illness was not corrected. Furthermore, the side effect including an electric shock from short-circuit, electric burns on physical tissues and the like caused even shunning of electrotherapy, whereby the purpose of treating diseases could not be attained.

SUMMARY OF THE INVENTION

The present invention, which was created to overcome the limit of therapeutic effect with conventional electrotherapeutic devices, is intended to provide human-body potential controlling electrotherapeutic device using both poles wherein a safe use by any one is possible due to the freeness from short-circuit even in the case of using two or multiple poles, a reduction in treating time and a maximized treating effect is obtained by increasing the number of the poles as required and the intra-cellular ionic passages can be activated to remove the source material for illness by binding and neutralizing the incomplete ions as the illness causing material, maldistributed excessively in physical tissues and in and out of the cell membranes, so that the diseases may be cured and prevented as well as human health can be improved.

BRIEF DESCRIPTION OF THE DRAWINGS

FIGS. 4a and 4b show the overall arrangement for three human-body potential controlling electrotherapeutic devices according to the first embodiment of the invention, linked in parallel, wherein FIG. 4a shows a schematic view of the circuit linked in parallel and FIG. 4b shows the schematic external appearance.

DETAILED DESCRIPTION OF THE INVENTION

Figure 1:
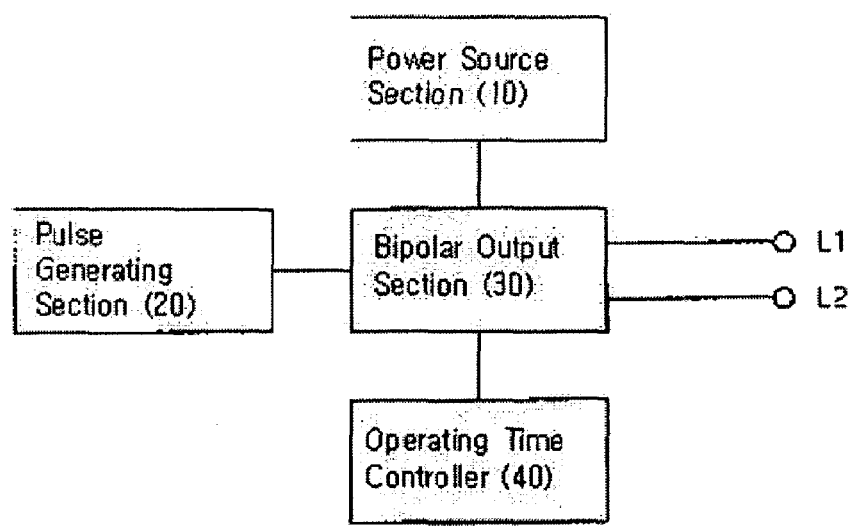
FIG. 1 shows schematically the first embodiment of the human-body potential controlling electrotherapeutic device according to the invention.

A human-body potential controlling electrotherapeutic device according to an embodiment of the invention, which includes power source sections 10 for supplying prescribed DC power to circuit sections after bridge rectifying commercial AC power, pulse generating sections 20 for inputting prescribed high voltage oscillating frequence signals to bipolar output sections after adjusting pulse generation frequencies, bipolar output sections 30 capable of selecting poles according to switching operation after amplifying and waveform shaping the signals output from said pulse generating sections 20, and an operating time controlling section 40 with alarm function, is characterized in that said power source section 10 and pulse generating section 20 are separately provided for each pole and the output terminals of the bipolar output sections 30 are each provided with a resistance and a triangular or pulse wave form generator, whereby short circuit is prevented, and simultaneous selection of various combination of two poles, such as (+)(−), (−)(−) and (+)(+), is possible, and further units each including a power source sections 10, pulse generating sections 20, bipolar output section 30 are connected parallel together with an operating time controlling section 40 to enable simultaneous selection of two or more poles.

The main reason that short-circuit is prevented in the inventive electrotherapeutic device having the characteristic features as described above is considered to be caused by the fact that power source section 10 and pulse generating section 20 are separately provided for each pole and further one pole at the output end of the bipolar output section 30 is provided with resistance to effect retardation and the other pole is provided with triangular- or pulse wave form generator to effect variation in output waves.

Further, the above-described object is also achieved by a human-body potential controlling electrotherapeutic device comprising a power section for bridge rectifying a commercial alternate current and for supplying a pre-determined direct current to circuit sections, a CPU for controlling general operations, display section for displaying set operations, control section for inputting control signals, buzzer section for producing buzz at the time of start and end of operations for equipments and at the time of inputting control signals, output regulating section for regulating the intensity of output, pulse generating section for inputting pre-determined oscillating frequency signals to an output section after regulating pulse-generating frequency and output section having plural output stages, wherein said output section is provided with separate transformers and independent rectifying circuit sections for respective output stages for producing single-polar outputs, and wherein plural sets each consisting of the pulse generating stages provided in the pulse generating section and the output section are arranged in parallel for permitting a simultaneous selection of plural polarities.

The invention is described in detail below by referring to the accompanying drawings.

<First Embodiment>

FIG. 1 shows schematically the first embodiment of the human-body potential controlling electrotherapeutic device comprising a power source section 10, a pulse generating section 20, a bipolar output section 30 and an operating time controlling section 40 for controlling the output time of the bipolar output section 30.

Figure 2A:
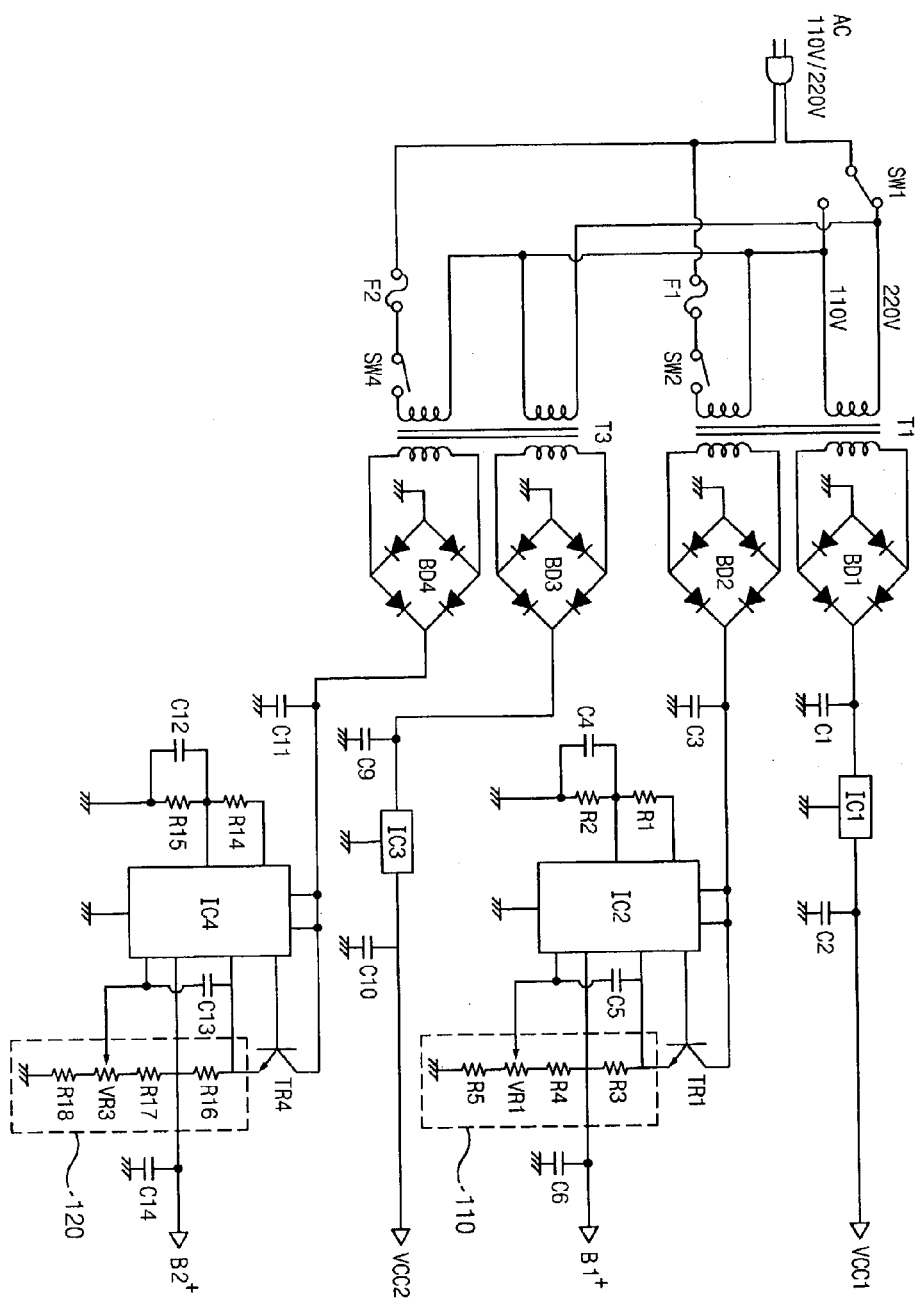
FIGS. 2a to 2c show the circuit diagrams of a physical potential controlling electrotherapeutic device according to the invention, wherein FIG. 2a relates to the power section, FIG. 2b to the pulse generating section and FIG. 2c to the both poles outputting section.

FIG. 2a shows the circuit arrangement for the above-described power source section 10, which includes a power selection switch SW1 for 110V/220V, a transformer circuit T1 to be connected to the output terminal L1 of the bipolar treating device shown in FIG. 1, and another transformer circuit T2 in parallel connection with the circuit T1 and to be connected to the other output terminal L2 of the treating device. The circuit described above for connection to the output terminal L1 comprises a power switch SW2 and a fuse F1 on the primary side of the transformer T1, a bridge circuit on the secondary side of the transformer T1 with a bridge diode BD1, condensers C1 and C2 and a regulator IC1 to output DC power VCC1, and the other bridge circuit on the secondary side of the transformer T1 with a bridge diode BD2, condensers C3~C6, a constant voltage integrated element IC2, a transistor TR1 and resistances R3~R6 to output DC power B1+. Hereupon, the condensers C4 and C5 and resistances R1 and R2 are to meet the specification of the constant voltage integrated element IC2.

The transformer circuit T3 in parallel connection with the transformer circuit T1 for the output terminal L1 and for connection to the output terminal L2 is arranged in the same manner as the transformer circuit T1 for the output terminal L1, so that the description thereof may be omitted.

Figure 2B:
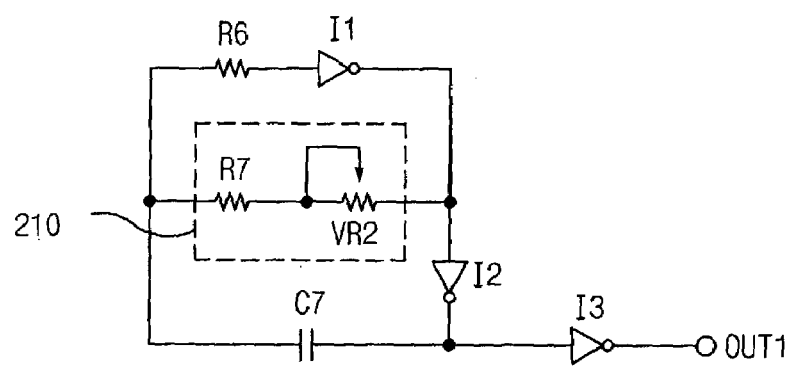
Figure 2B:
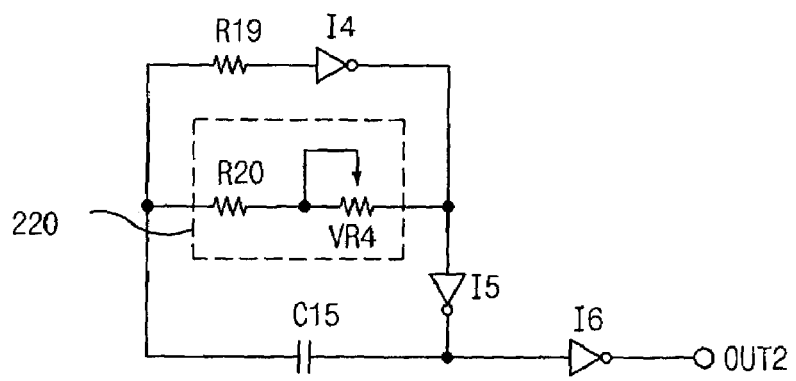

FIG. 2b shows the circuit for a pulse generating section 20, wherein the circuit having the output OUT1 includes resistances R6 and R7, a condenser C7, inverters I1~I3 and a variable resistance VR2, while the circuit having the output OUT2 includes resistances R19 and R20, a condenser C15, inverters I4~I6 and a variable resistance VR4.

Figure 2C:
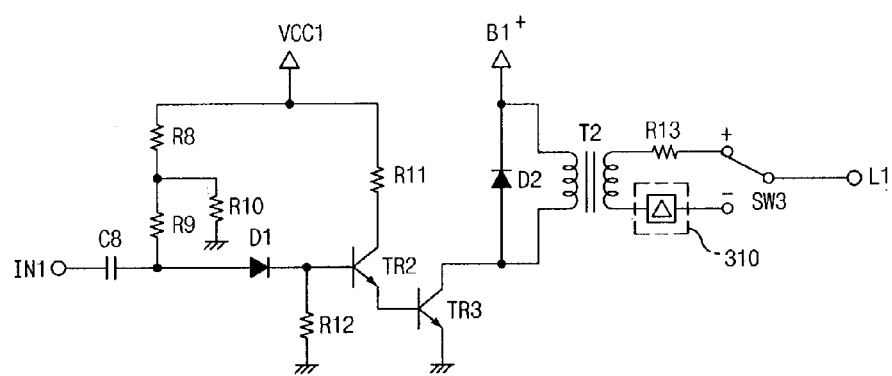
Figure 2C:
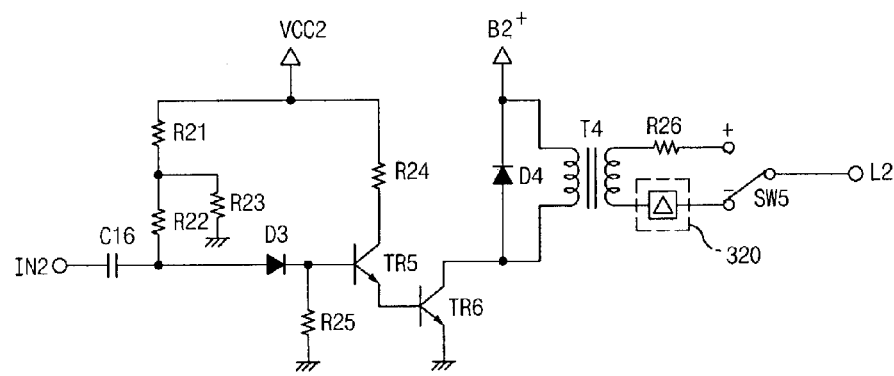

FIG. 2c is the circuit diagram of the bipolar output section 30 capable of outputting two poles such as (+)(−), (+)(+), (−)(−), wherein an oscillating frequency output signal OUT1 from the pulse generating section 20 is applied on an input terminal IN1, on the primary side of a transformer T2 diodes D1 and D2, resistances R8~R12, a condenser C8 and transistors TR2 and TR3 for amplifying voltage signals are connected, and on the secondary side of the transformer T2 a resistance R13, the first triangular wave form generator 310 and a pole selection switch SW3 are connected, so that the voltage of the pole selected as the output terminal L1 may be output. In the same manner a signal from an oscillating frequency signal output OUT2 from the pulse generating section 20 is applied on an input terminal IN2, on the primary side of a transformer T4 diodes D3 and D3, resistances R21~R25, a condenser C16 and transistors TR5 and TR6 for amplifying voltage signals are connected, and on the secondary side of the transformer T4 a resistance R26, the second triangular wave form generator 320 and a pole selection switch SW5 are connected, so that the voltage of the pole selected as the output terminal L2 may be output.

Figure 3A:
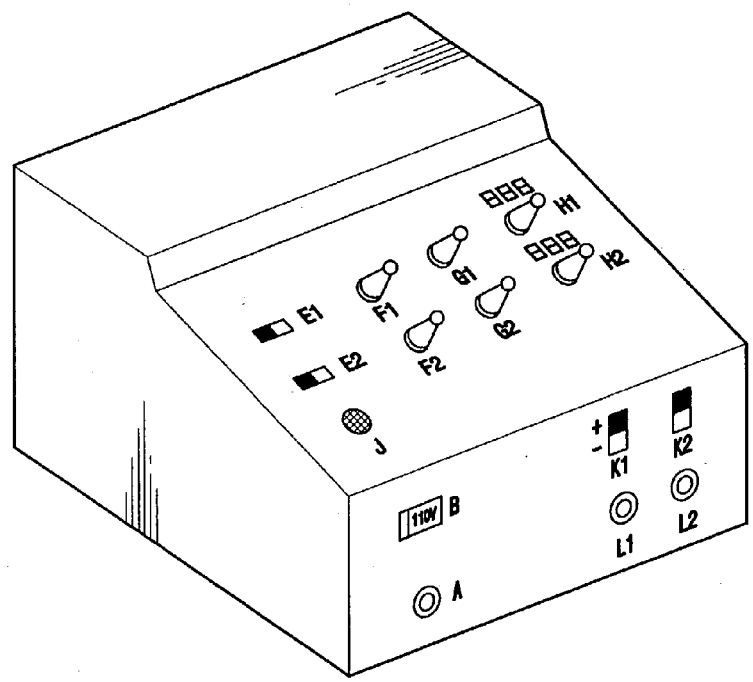
FIG. 3a shows the illustrative external appearance of a human-body potential controlling electrotherapeutic device according to the invention.

Referring FIG. 3a, the power input terminal is indicated by A, the switch to select the power of 110V or 220V by operating the power selection switch SW1 shown in FIG. 2a is shown as B, and the symbols E1 and E2 represent the power switches corresponding to SW2 and SW4 in FIG. 2a to turn on the power. The keys F1 and F2 serve to adjust the output voltages respectively by varying the resistance values of the variable resistances VR1 and VR3 for the first and second voltage adjusting sections 110 and 120 in FIG. 2a. The keys G1 and G2 are used respectively to adjust the output periods corresponding to 300 to 500 Hz by varying the resistance values of the variable resistances VR2 and VR4 for the first and second output frequency adjusting sections 210 and 220 in FIG. 2b for the pulse generating section 20. Furthermore, the keys H1 and H2 represent operating time setters to define the operating duration of a human-body potential controlling electrotherapeutic device by manually setting the time between 0 and 60 minutes for example, whereas the alarm for indicating the end of the set operating time is shown as J. Switches K1 and K2 are used to select the positive(+) or negative(−) pole for the human-body potential controlling electrotherapeutic device. As the switches K1 and K2 correspond to the switches SW3 and SW5 in the bipolar output section 30 shown in FIG. 2c, a directional operation of the key K1., for example, would cause the switch SW3 to select a specific pole at the output terminal L1. The terminals L1 and L2 represent respectively the voltage output terminals for the human-body potential controlling electrotherapeutic device.

Figure 3B:
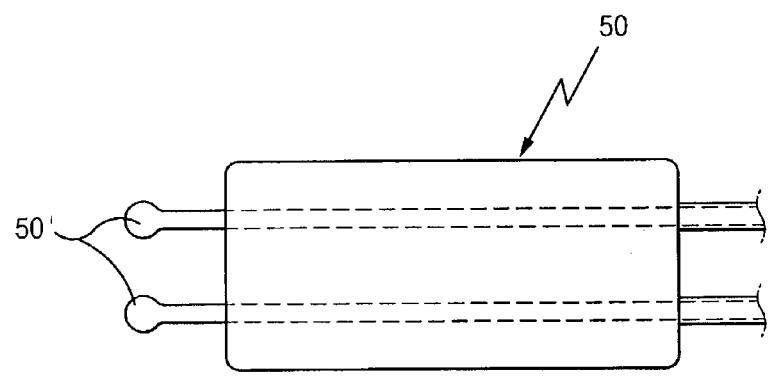
FIG. 3b shows the illustrative construction for a therapeutic part incorporatable in a human-body potential controlling electrotherapeutic device according to the invention.

FIG. 3b illustrates an arrangement of a treating part 50 which can be applied in the human-body potential controlling electrotherapeutic device according to the invention and which is provided with two round-ended treating rods 50', so that two poles can be contacted with human body simultaneously during treatment by connecting the treating part 50 to the output terminals L1~L6.

Figure 3C:
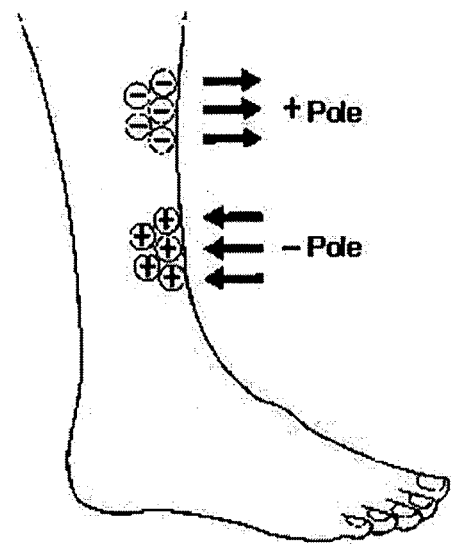
FIG. 3c shows the state at the time of treating a disease of human body under use of a human-body potential controlling electrotherapeutic device according to the invention.

FIG. 3c illustrates symbolically the principle of treating a disease through ionic harmonization by using the human-body potential controlling electrotherapeutic device according to the invention, wherein it is seen that anions accumulated in a human body are discharged to the outside by bringing the positive(+)-charged pole of the treating rods 50' in a treating part 50 in contact with the anion-concentrated area, while the contact of the negative(−)-charged rod in the treating part 50 causes the electric charge to penetrate cations concentrated in the human body to neutralize the latter, so that the disease may be cured.

Figure 4A:
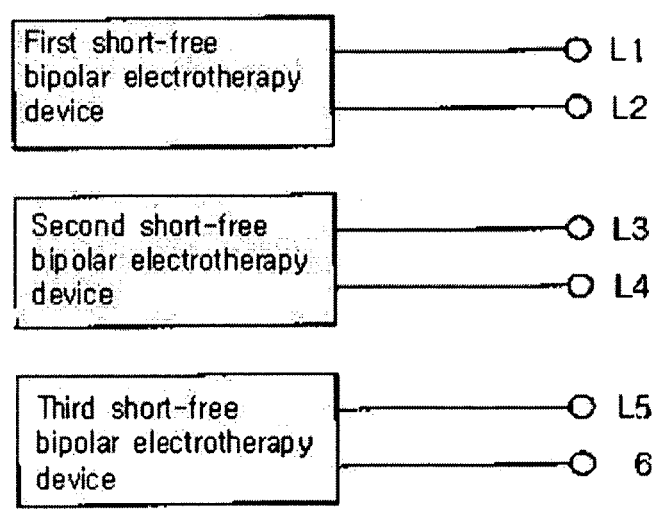

FIG. 4a shows schematically the human-body potential controlling electrotherapeutic device in parallel connection according to the invention, wherein the output terminals of the treating devices 1~3 are indicated as L1~L6.

Figure 4B:
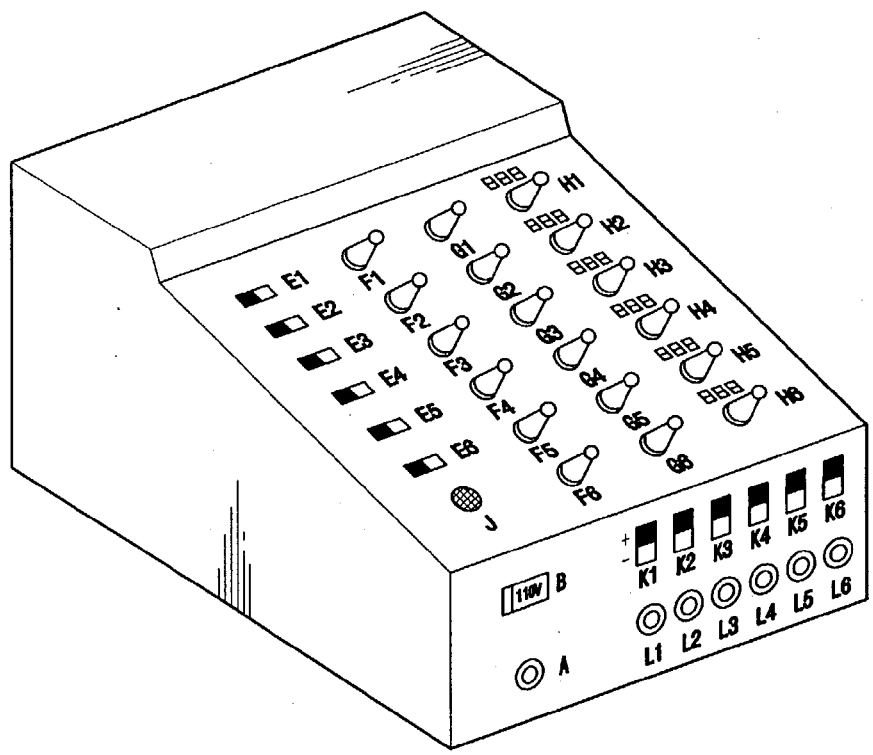

FIG. 4b shows the outward view of human-body potential controlling electrotherapeutic device in parallel connection according to the invention representing an enlargement of the corresponding one shown in FIG. 3. The symbols A and B stand for the power input terminal and 110 V/220 V power selection switch respectively and the symbols E1~E6 stand for the power switches for respective output terminals L1~L6 of an inventive human-body potential controlling electrotherapeutic device. In addition, the symbols F1~F6 stand for the switches for adjusting the output voltages and the symbols G1~G6 for the output cycle adjusting switches. The symbols H1~H6 stand for the operating time pre-setters to define output operating time and the alarm signifying the elapse of the preset operating time is indicated by J. Moreover, the symbols K1~K6 represent the switches for selecting either the positive(+) or negative(−) pole for the inventive human-body potential controlling electrotherapeutic device and the symbols L1~L6 represent the voltage output terminals respectively for the treating device.

The operation of the circuit according to the invention, constructed as described above, is described in the following.

First, referring to the power source section 10 as shown in FIG. 2a, selection of either 110V or 220V AC power at the power selection switch SW1 followed by switching on the power switch SW2 and/or SW4 causes the induction of prescribed voltage on the secondary side of the transformer T1 and/or T3. The induced power is rectified through the bridge diode BD1 and/or BD3 and the smoothing condenser C1 and/or C9 and applied to the regulator IC1 and/or IC3 for supplying the output power, lower than the input power but stabilized, in order to provide the board power VCC1 and/or VCC2. Additionally, the power induced as described above on the secondary side of the transformer T1 and/or T3 is applied through the bridge diode BD2 and/or BD4 and the condenser C3 and/or C11 to the constant voltage integrated circuit IC2 and/or IC4 to output a prescribed DC power B1+ and/or B2+ by effecting variation in the transistor TR1 and/or TR4 and adjusting the variable resistance VR1 and/or VR3 in the output voltage adjusting section 110 and/or 120. The DC power B1+ and/or B2+ is supplied to the primary side of the transformer T2 and/or T4 in the bipolar output section 30 as shown in FIG. 2c.

Referring to the circuit arrangement for the pulse generating section 20 as shown in FIG. 2b, pulse signals having prescribed oscillating frequencies are generated with the help of the resistances R6, R7; R19, R20, the condenser C7; C15 and the inverters I1~I3; I4~I6, wherein the adjustment in the frequencies of generated oscillating pulse signals can be made by regulating the variable resistances VR2; VR4 in the output frequency adjusting section 210; 220. The pulse signals with prescribed oscillating frequencies, adjusted as above, are applied respectively to the input terminal IN1; IN2 of the bipolar output section 30 shown in FIG. 2c through the output terminal OUT1; OUT2.

The pulse signals having prescribed oscillating frequencies, applied to the bipolar output 30, are shaped in wave form through the diode D1; D3 and applied on the primary side of the transformer T2; T4 after amplification by the transistors TR2, TR3; TR5, TR6. The voltages induced on the secondary side of the transistor T2; T4 lead either to the resistances R13; R26 on the positive pole or to the triangular wave form generating section 310; 320 on the negative side and are output through respective output terminals L1~L6 after selecting the polarities through operation of the output selection switches SW3; SW5.

Referring to the human-body potential controlling electrotherapeutic device in parallel connection shown in FIG. 4a, use of multiple poles is possible by switching on the switches E1~E6, adjusting the output voltage adjusting means F1~F6 and output cycle adjusting means G1~G6, operating the pole selection switches K1~K6 and adjusting the operating time setting means H1~H6.

Because in the human-body potential controlling electrotherapeutic device, each pole is provided with the power source section and pulse generating section, and each plus pole before the pole selection switch SW3; SW5 of the bipolar output section 30 is provided with the resistance R13; R26 while each minus pole is provided with the triangular wave form generating section 310; 320, the risk of shirt circuit which was pointed out as a major disadvantage with the prior art is prevented due to the voltage difference between poles, the change with time in output wave forms and the variation of the wave forms, no matter which poles are selected and output. Although in FIG. 2c, the plus poles at the output terminals were connected to resistances and the minus poles were connected to triangular wave form generators, the arrangement may be reversed, that is, the plus poles connected to wave form generators and the minus poles to resistances may be possible. Otherwise, the plus pole of one output terminal connected to resistances, the minus pole of the same output terminal connected to the triangular wave form generator, the plus pole of the other output terminal connected to the triangular wave form generator and the minus pole of the same other output terminal connected to resistances may also be possible. Naturally, the reverse is possible. The pulse wave beside the triangular wave can be employed.

Although human-body potential controlling electrotherapeutic device in parallel connection were described in the embodiment shown in FIG. 4a, the number of incorporated treating devices is not limited thereto, so that more than three treating devices may be assembled in a parallel manner if possible. Instead of the circuit of parallel connection before the transformer T1 in FIG. 2a, a more simplified circuitry could be created to thereby realize a bipolar treating device.

As discussed above, the present invention, in which each output circuit for a pole is provided with a power source and a pulse generator and an output terminal can be connected to either resistances or to a triangular or pulse form generator, can have not only the physical effect as expected for conventional electrical treating devices but also the effect of eliminating the danger from shirt-circuit by taking advantage of the time difference between two poles and the variation in wave forms, and furthermore, thanks to the use of two poles, can remove the pathogenic elements caused by the unbalanced potentials, and allows selective application of two or multiple poles onto abnormal affected areas as required, so that the therapeutic effect depending on different areas and different diseases may be maximized. In other words, human-body potential controlling electrotherapeutic device having two output poles may be used at homes, while human-body potential controlling electrotherapeutic device having more than two output poles may be used in places requiring large demands, such as hospitals, so that a large number of patients can be treated simultaneously. Even for a single patient, treating time can be shortened remarkably, for example by several times as compared to the conventional cases, because many morbid areas can be treated at the same time.

The present invention should not be bound by any theories or grounds based on them, presented or suggested in the above description.

Moreover, it is to be understood that, while the invention was described mainly with respect to specific embodiments, the invention is never restricted to those embodiments and a variety of modifications and alterations would be possible to a man skilled in the art by referring to the description or drawings presented here and within the spirit of the invention and thus those modifications or alterations are to fall within the scope of the invention, which scope should be limited only by the attached claims.

<Second Embodiment>

Figure 5:
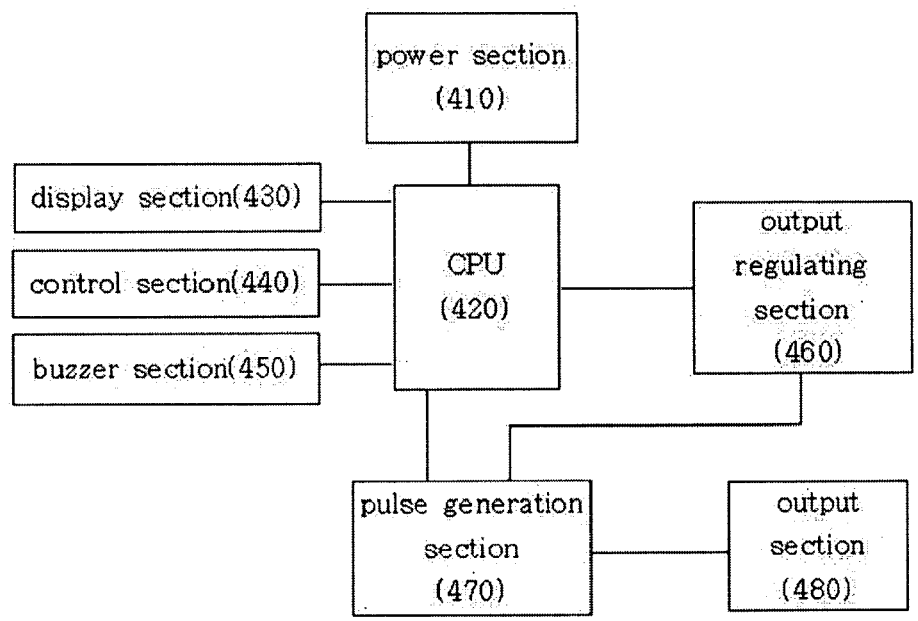
FIG. 5 shows schematically the second embodiment of the human-body potential controlling electrotherapeutic device according to the invention.

FIG. 5 shows schematically the second embodiment of human-body potential controlling electrotherapeutic device according to the invention and comprises a power section 410, CPU 420, display section 430, control section 440, buzzer section 450, output regulating section 460, pulse generating section 470 and output section 480 consisting of plural independent full-wave or half-wave rectifying circuits 481, 482.

The power section 410 supplies pre-determined DC power rectified from the commercial AC power to respective circuit sections.

The display section 430 displays operations as set for human-body potential controlling electrotherapeutic device according to the invention.

Further, the control section 440 functions to input the control signal in accordance with the operations of human-body potential controlling electrotherapeutic device according to the invention, when the operations are set by a user.

The buzzer section 450 produces buzz sound when control signals are input by users and when the electrotherapy device according to the invention perform operations.

The above-described pulse generating section 470 generates predetermined oscillating frequency signal to output it to the output section 480. These pulse generating sections are individually provided for respective output stages of output section 480.

The output section 480 is provided, at its each output stage, with a transformer T5, T6 as well as a full-wave or half-wave rectifying section 481, 482, whereby respective independent output circuits are provided.

The above-described output regulating section 460 regulates the output entering the output section 480.

The CPU 420 controls operation of respective parts.

Plural sets of the output section 480 and pulse generating section 470 can be arranged in parallel to thereby output a multitude of poles.

Figure 6:
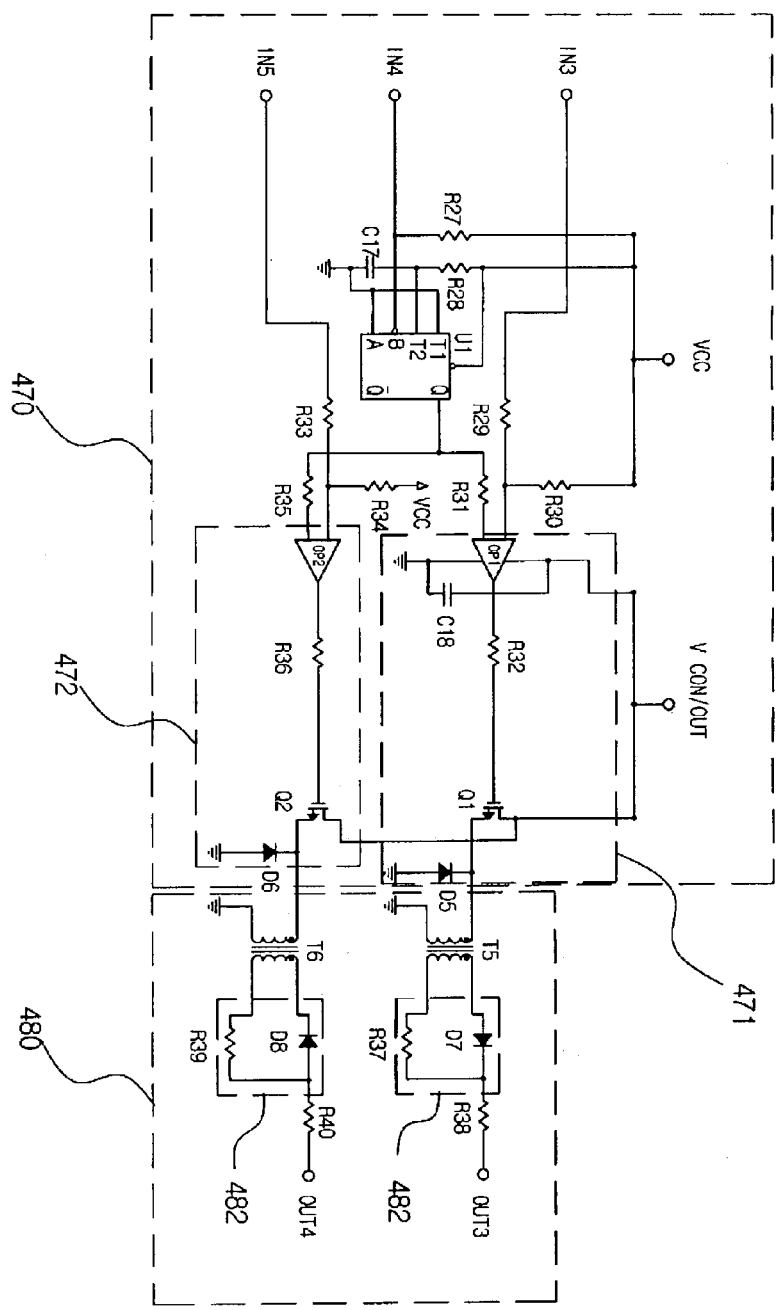
FIG. 6 shows the circuit diagram of a pulse generating section and output section according to the second embodiment of the human-body potential controlling electrotherapeutic device according to the invention.

FIG. 6 shows the circuit of the pulse generating section 470 and output section 480 of the second embodiment of the electrotherapy device according to the invention.

The pulse generating section 470 comprises input terminals IN3, IN4, IN5 for receiving frequency generating signals through the CPU 420, and an amp circuit OP1, OP2 for amplifying the frequency generating signals to a pre-determined level and transistor circuits Q1, Q2 for producing pulses, wherein the output section 480 includes transformers T5, T6 for receiving pulse signals output from the pulse generating stages 471, 472 of the pulse generating section 470 and for converting the received signals into alternate current, half-wave rectifying circuit sections 481, 482 for providing signals having only one polarity from (+), (−) alternate current signals from the transformers and output terminals OUT3, OUT4 for outputting signals to be applied to a human body.

In particular, VCC stands for the basic voltage input from the power section 410 and VCON/OUT for the output regulating voltage input to the pulse generating section 470 from the output regulating section 460.

The frequency generating signal to input terminals IN3, IN4, IN5 from the CPU 420 is amplified to a predetermined level through amp circuits OP1, OP2 of pulse generating stages 471, 472. The trigger circuit U1 where the above-described signal is jumped to a finite width for the purpose of exact operation of the signal is connected to the amps OP1, OP2. Herein, R27, R28, R29, R30, R33, R34, R35 stand for resistors to regulate the measure of input voltages and C17 represents a capacitor provided in the trigger circuit U1.

The capacitor C18 connected to the amp OP1 acts to modulate the signals input to transistors Q1 and Q2 so as to be different from each other. R32 and R36 act to reduce the size of the signals input to transistors Q1 and Q2 so as not to exceed the input limit of the transistors Q1, Q2.

D5 and D6 are intended to protect the circuit in the case of overload being applied, while R38 and R40 are to increase or decrease the output voltage.

The operation of the embodiment of the invention constructed as described above is described below.

First, when the frequency generating signal enters the input terminals IN3, IN4, IN5 after having left the CPU 420, the signal is input in transistors Q1, Q2 after it is amplified to a pre-determined level in the amp circuits OP1, OP2 of the pulse generating stages 471, 472. If the potential of this signal exceeds the minimum potential or threshold value as would be required to actuate the transistors Q1, Q2, the transistors are turned on, and otherwise they are turned off. This on-off operation of the transistors Q1, Q2 causes the generation of pulses, the size of which pulses are adjusted dependent on the size of VCON/OUT.

The pulses so generated are input to the transformers T5, T6 to be converted into alternate currents, whereby independent circuits now result, as seen in FIG. 6.

The transformer T5 is provided with a half-wave rectifying circuit section 481 which operates in positive(+)-phase so that (+) half-wave alternate current may be output at the output terminal OUT3, while the transformer T6 is provided with a half-wave rectifying circuit section 482 which operates in negative(−)-phase so that (−) half-wave alternate current may be output at the output terminal OUT4.

Accordingly, the output section 480 having half-wave rectifying circuit sections 481, 482 for respective transformers T5, T6 outputs single polar currents.

The half-wave rectifying circuit sections 481, 482 are arranged in parallel, consisting of diodes D7, D8 and resistors R37, R39.

Figure 7:
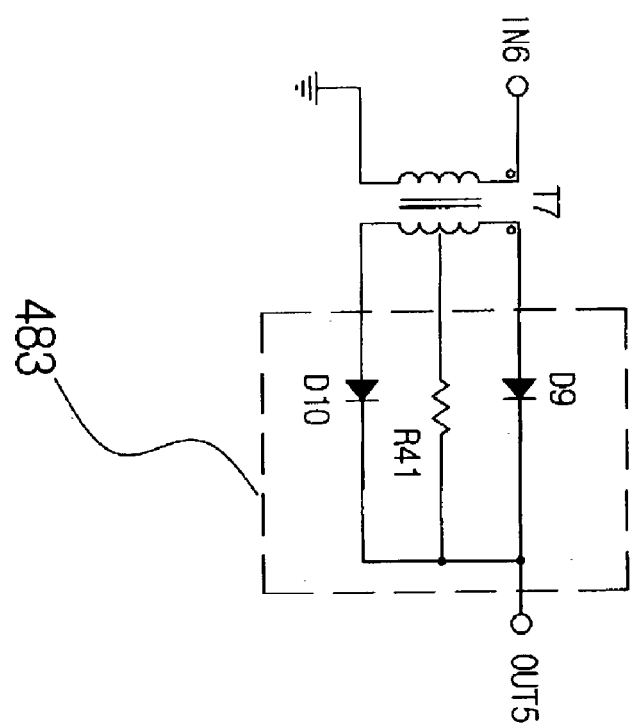
FIG. 7 shows the circuit diagram of the output section having a full-wave rectifying circuit according to the second embodiment of the human-body potential controlling electrotherapeutic device according to the invention.

FIG. 7 shows an output section 480 with a full-wave rectifying circuit according to the second embodiment of the invention, which can be applied to the human-body potential controlling electrotherapy device according to the invention by regulating the output voltage of a full-wave rectifying circuit section 483.

The signal which left the pulse generating stages 471, 472 of the pulse generating section 470 enters an input terminal IN6 and passes a transformer T7 before going through diodes D9, D10 and a resistor R41, so that a (+) full-wave rectification signal can be output at an output terminal OUT5.

A (−) full-wave rectification signal can be produced simply by reversing the in and output direction of the diodes relative to the plus case and therefore further description is omitted.

In the above description, although the output section 480 with half-wave rectifying circuits 481 and 482 for (+) polar and (−) polar outputs were mainly illustrated, a full-wave rectifying circuit 483 can be employed if need be, as mentioned and furthermore there may be provided an bipolar output section 480 in which full-waves of (+, +) and (−, −) are output. Still further, a parallel connection of plural output stages each including a transformer and rectifying circuit can produce multiple output such as (+, −, +, −, +) etc.

As discussed above, the present invention, which takes the advantage of the time difference of both poles and change in wave form resulting from the provision of pulse generating sections and transformers for respective output stages and arrangement of full-wave or half-wave rectifying circuits on respective output stages, can not only have the physical or medical effect expected from conventional electrotherapeutic appliances but also can remove the risk of short circuit, and additionally based on the use of both poles, can eliminate pathogenic elements caused by the unbalance in electric potentials, and furthermore can maximize the therapeutic efficacy dependent on affected parts and the kind of diseases by selection of both poles or multi-poles as required by morbid parts. General homes may choose the type of electrotherapeutic device having two output poles, while for high use applications like hospitals or clinics, electrotherapeutic devices having more than two output poles may be used, so that a number of patients may be treated simultaneously or otherwise even a single patient may be treated on various morbid parts at the same time, whereby treating duration may be shortened by several times the duration required for the case with a conventional appliance and on the other hand, portable appliances may be realized by reducing the size.

What is claimed is:

1. A human-body potential controlling electrotherapeutic device including power source sections (10) for supplying prescribed DC power to circuit sections after bridge-rectifying commercial AC power, pulse generating sections (20) for inputting prescribed high-voltage oscillating frequency signals to bipolar output sections after adjusting pulse generation frequencies, and bipolar output sections (30) capable of selecting poles according to switching operation after amplifying and waveform-shaping the signals output from said pulse generating sections (20), and further an operating time controlling section (40) with alarm function, wherein said power source section (10) and pulse generating section (20) are separately provided for each pole and the output terminals of the bipolar output sections (30) are each provided with a resistance and a triangular pulse wave form generator, whereby short circuit is prevented.

2. A human-body potential controlling electrotherapeutic device according to claim 1, wherein the power source section (10), the pulse generating section (20) and the bipolar output section (30) having the resistance and the triangular pulse wave form generator at its output terminal are provided separately on each pole, and plural sets each including the power source section (10), the pulse generating section (20) and the bipolar output section (30) are connected in parallel together with the operating time controlling section (40), so that simultaneous selection of plural poles may be possible.

3. A human-body potential controlling electrotherapeutic device comprising a power section (410) for bridge-rectifying a commercial alternate current and for supplying a pre-determined direct current to circuit sections, a CPU (420) for controlling general operations, display section (430) for displaying set operations, control section (440) for inputting control signals, buzzer section (450) for producing buzz at the time of start and end of operations for equipments and at the time of inputting control signals, output regulating section (460) for regulating the intensity of output, pulse generating section (470) for inputting pre-determined oscillating frequency signals to an output section after regulating pulse-generating frequency and output section (480) having plural output stages, wherein said output section (480) is provided with separate transformers(T5, T6) and independent rectifying circuit sections (481, 482) for respective output stages for producing single-polar outputs, and wherein plural sets each consisting of the pulse generating stages(471, 472) provided in the pulse generating section (470) and the output section (480) are arranged in parallel for permitting a simultaneous selection of plural polarities.

4. The device as defined in claim 3, wherein said rectifying circuit section comprises a full-wave rectifying circuit section (483) or half-wave rectifying circuit sections (481, 482).

5. A human-body potential controlling electrotherapeutic device including power source sections (10) for supplying prescribed DC power to circuit sections after bridge-rectifying commercial AC power, pulse generating sections (20) for inputting prescribed high-voltage oscillating frequency signals to bipolar output sections after adjusting pulse generation frequencies, and bipolar output sections (30) capable of selecting poles according to switching operation after amplifying and waveform-shaping the signals output from said pulse generating sections (20), and further an operating time controlling section (40) with alarm function, wherein said power source section (10) and pulse generating section (20) are separately provided for each pole and the output terminals of the bipolar output sections (30) are each provided with a resistance and a triangular pulse wave form generator, whereby short circuit is prevented, wherein the power source section (10), the pulse generating section (20) and the bipolar output section (30) having a resistance and the triangular pulse wave form generator at its output terminal are provided separately on each pole, and plural sets each including the power source section (10), the pulse generating section (20) and the bipolar output section (30) are connected in parallel together with the operating time controlling section (40), so that simultaneous selection of plural poles may be possible.

* * * * *